United States Patent [19]

Hynes, Jr.

[11] 4,105,923
[45] Aug. 8, 1978

[54] PATIENT HANDLING SYSTEM AND APPARATUS FOR TOMOGRAPHIC SCANNING

[75] Inventor: John L. Hynes, Jr., Columbia, Md.

[73] Assignee: Pfizer Inc., New York, N.Y.

[21] Appl. No.: 783,556

[22] Filed: Apr. 1, 1977

[51] Int. Cl.$^2$ ............................ A61B 6/04; A61G 13/00
[52] U.S. Cl. ................................ 250/456; 250/445 T; 269/322
[58] Field of Search ................... 250/445 T, 439, 456, 250/453, 444; 269/322, 323, 328

[56] References Cited

U.S. PATENT DOCUMENTS

4,017,737   4/1977   Hudson .............................. 250/453

Primary Examiner—Alfred E. Smith
Assistant Examiner—T. N. Grigsby
Attorney, Agent, or Firm—Connolly and Hutz

[57] ABSTRACT

The patient is transported to the tomographic scanner on a cart which incorporates a longitudinally movable pallet section which is locked on top of the cart until the cart is engaged with an elevating island in front of the scanner. The island is elevated under the cart to lift it off the floor on a frame, which is securely locked to the cart. The pallet then becomes released for longitudinal movement. When the pallet is raised into alignment with the scanning tunnel, it is engaged with a longitudinal traversing drive which moves the pallet and patient into the scanning position with the extended pallet resting upon the rear pallet support board. All portions of the pallet disposed in the path of scanning X-rays are translucent to such rays. The cart cannot be released from the island until the pallet is fully retracted and the cart lowered to the floor. A plurality of carts such as two or three may be provided to permit patients to be prepared for and deprepared from scanning while a patient is being scanned, thus maximizing utilization of the scanner in a given time period.

21 Claims, 13 Drawing Figures

PATIENT HANDLING SYSTEM AND APPARATUS FOR TOMOGRAPHIC SCANNING

BACKGROUND OF THE INVENTION

Patients to be X-rayed on a tomographic scanner must be accurately vertically and horizontally positioned relative to the scanning tunnel and apparatus. Heretofore, all of such positioning apparatus has been permanently mounted relative to the scanner. The patients have been transported to the scanner on conventional hospital carts, necessitating considerable time to transfer the patient to the positioning apparatus and to adjust the patient to the required position upon it. This requires a multiplicity of transfers of the patient, and considerable machine time is consumed therein. An object of this invention is to provide an efficient patient handling system and apparatus for use in conjunction with a tomographic scanner which minimizes handling and transferring of the patient to be scanned and maximizes the scanning time available from the scanner.

SUMMARY OF THE INVENTION

In accordance with this invention the patient is transported to the scanner on a cart which incorporates a longitudinally movable pallet section which is locked on top of the cart until the cart is engaged with an elevating island in front of the scanner. The island is elevated under the cart to lift it off the floor on a frame which is securely locked to the cart. The pallet then becomes released for longitudinal movement. When the pallet is raised into alignment with the scanning tunnel, it is engaged with a longitudinal traversing drive, which moves the pallet and patient into the scanning position with its extended end resting upon the rear pallet support. All portions of the pallet disposed in the path of scanning X-rays are translucent to such rays. The cart cannot be released from the island until the pallet is fully retracted and the cart lowered to the floor. A plurality of carts, such as two or three, may be provided to permit patients to be prepared for and deprepared from scanning while another patient is being scanned, thus maximizing utilization of the scanner in a given time period. A magnetic docking apparatus is provided for immobilizing this cart when disengaged from the scanner.

BRIEF DESCRIPTION OF THE DRAWINGS

Novel features and advantages of the present invention will become apparent to one skilled in the art from a reading of the following detailed description in conjunction with the accompanying drawings wherein similar reference characters refer to similar parts and in which.

DESCRIPTION OF THE PREFERRED EMBODIMENT

Figure 1:
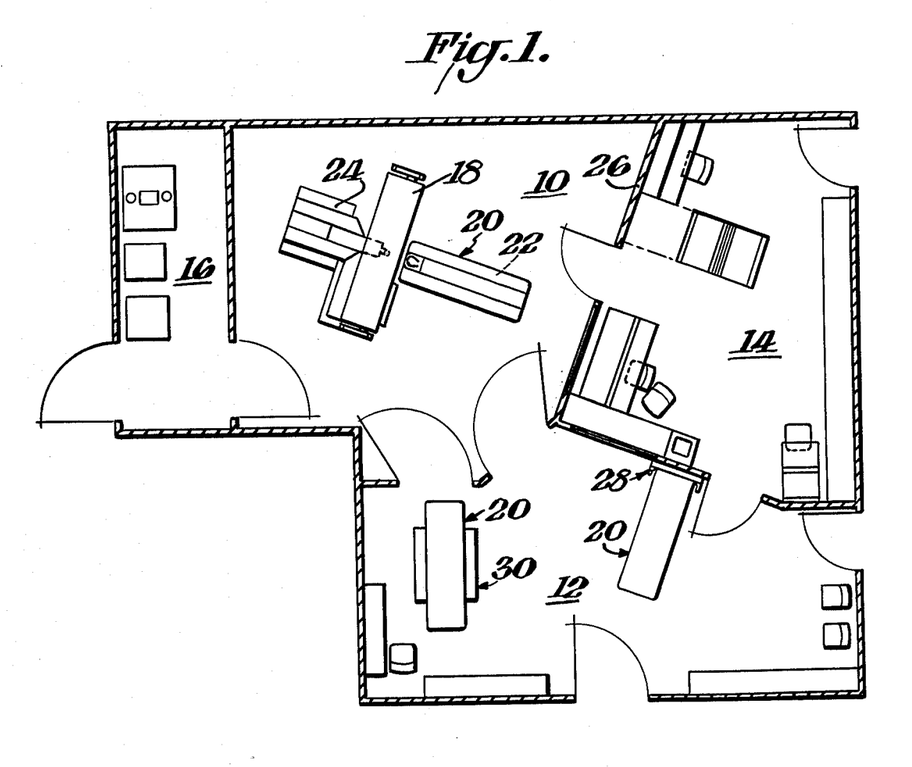
FIG. 1 is a plan schematic view of a tomographic scanner installation which shows one embodiment of the system of this invention, utilizing at least two carts for transporting and positioning the patient.

In FIG. 1 is shown an architectural layout of the installation for a tomographic scanner in which at least two disengageable carts are utilized for transporting patients to the scanner and positioning them relative to it. The operational requirements of the system are patient safety and comfort as well as efficient patient processing. The fulfillment of these requirements is dependent upon both the spatial layout of all the areas or rooms shown in FIG. 1 and the length of the major time segments of the CT scanning process. The operational research focuses upon the efficiency requirement. Efficiency is examined according to the three recommended plans and according to the patient throughput rates of each system.

PATIENT PROCESSING TIME SEGMENTS

Efficiency of the system is measured by the patient throughput rate. Since that rate is determined by many factors, it is necessary to divide the overall patient processing procedure into its principal time segments: preparation, scan, and depreparation. The scan time segment can be further subdivided into: entrance and alignment of cart, scan, and dealignment and exit of cart. The length of each of these time segments is affected by a variable time segment, contrast injection.

CONTRAST INJECTION

Research conducted on contrast protocol indicates that each time segment varies according to the point at which contrast is used and the length of time necessary to establish patient comfort.

Although contrast is generally used to enhance scans, it may be used in a variety of ways which affect overall patient processing efficiency. The protocol described below is used for the purpose of illustration and analysis. It is a more efficient method of administering contrast and preserves the operating efficiency of the system.

The recommendation is as follows: During the preparation, a saline IV should be started. The patient can then be wheeled into the scan room and the scanning begun. After a number of scans have been run, the technician or the doctor (as required by state law) can reenter the scan room and start the fast-drip contrast infusion. After a sufficient amount of time has passed for enhancement, scanning may be resumed.

Removing the patient from the scan room to administer the contrast injection is not recommended unless more than 20 minutes are required for proper enhancement. The decision of whether or not to remove a patient from the scanner room is based upon the time ratio of the principal time segments. This will be further examined in a later discussion concerning the efficiency of the three recommended system plans. There are three possible contrast protocols: contrast injection prior to scanning, which lengthens preparation time; contrast injection after a series of scans has been taken, which significantly increases the scan segment relative to the preparation and depreparation segments, or no contrast injection at all, in which case the preparation and/or scan segments remain at their minimum value.

Factors which delay the injection of contrast are the availability of appropriate staff and the condition of the patient. Availability of staff is optimized by including an office for the radiologist within the system. If available space cannot accommodate a radiological office, the system should be situated near the radiologist's offices and telephone or intercom should be provided between technician and radiologist. The physical condition of the patient determines the relative difficulty or ease of the injection process. Problems which are encountered are adverse reactions to contrast materials in the body and difficulty of injection in obese patients.

Whether a bolus type injection or a slow drip infusion is used will determine the extent of nausea, vomiting, or discomfort experienced by the patient.

FACTORS AFFECTING TIME SEGMENTS

Each time segment is affected by various factors. The following examine each of these factors in detail. The length of the preparation segment is affected by the relative location of the waiting area to the system. As you will see later in the Recommended Plans, both the two-cart and three-cart systems include a waiting area within the site of the system. The disposition of the patient to be scanned, including both age and condition, determine how long the preparation segment will be. Elderly persons and non-ambulatory persons require additional assistance and thus the overall preparation time is increased. Depending on the expected diagnosis of the patient, contrast may be injected during the preparation stage.

CART ALIGNMENT AND CART DEALIGNMENT

The major factor affecting the length of these two time segments is the type of system used. In the one-cart system, the mobile bed cart will most frequently remain stationary on the lift island. Although this eliminates the time required for adjustment of the cart and alignment with the lift island, the entire preparation and depreparation consequently occur at the scanner gantry and the lift island. The overall patient throughput rate is decreased significantly.

In the two-cart and three-cart systems, a fairly regular time value for alignment and dealignment will be observed. The time value is affected by the placement of the entry doors. Doors placed in front of the mobile bed cart provide smooth maneuvering to the scanner gantry. The angle of approach of the carts to the lift island also affects the relative ease or difficulty of maneuvering the carts to the lift island.

SCAN TIME

Scan time is determined by the total number of scans required and by the protocol for the use of contrast. Alignment of the patient on the bed cart relative to the gantry is accomplished at the control console by the technician. The completion of the scan segment is dependent upon the availability of the radiologist to review the scans. In some cases, a radiologist may determine that more scans are required for accurate diagnosis.

DEPREPARATION

The depreparation of the patient is dependent upon the availability of the technician. The patient processing system will run smoothly in a two-cart system if there are two technicians and each one follows through the entire preparation, scanning, and depreparation of one patient. In the three-cart system, the use of only two technicians for three patients in the system will require patients to be waiting at various stages of preparation and depreparation.

PREPARATION AND DEPREPARATION

The time intervals at which patients are scheduled for appointments affects the efficiency of the system and the comfort of the patient. It is helpful to schedule patients according to the usual processing time of the system. Patients should not have to wait long periods of time once they are in the preparation area, however, appointments should be scheduled so that patients are prepared in time to keep the scanner in use. The advantage of the mobile bed cart system is to have the patient at the scanner gantry only when the scanner itself can be used.

COMPARISON OF RECOMMENDED SYSTEMS

The processing of five patients is compared in the one-cart, two-cart, and three-cart systems. Patient processing is determined by the overall relationship of preparation, scan, and depreparation to each other. The use of the mobile bed cart system allows an overlap of the principal time segments for each patient. In the two-cart system, two patients can be in the system simultaneously: one patient in scan, and one patient in preparation or depreparation. The two-cart system has little flexibility in patient processing, since a third patient can enter the system for preparation only after the first is completely deprepared. The three-cart system allows for three patients in the system simultaneously. While one patient is in scan, two patients can be in either depreparation or preparation. The three-cart system is the most efficient allowing the greatest flexibility in processing time. In the two-cart system, there is less flexibility in the time allowed for preparation of patients.

The best and worst patient processing times are estimated from on-site observation. The two-cart system will operate as efficiently as the three-cart system when the preparation, scan, and depreparation segments remain at the best possible time values. However, the two-cart system develops delays when the worst possible time values occur.

The installation for a two-cart system shown in FIG. 1 includes a scanning room 10, a preparation and depreparation room 12, a control room 14 and a utility room 16. Tomographic scanner 18, which is for example of the type described in U.S. Pat. Nos. 3,922,552 and 4,005,311, is shown in scanning room 10 with cart 20 engaged with elevating island 22 and rear pallet support 24 for scanning a patient (not shown) lying on cart 20.

Operating technicians (not shown) control the scanning operation from control room 14. Within it they are shielded by lead wall 26 while X-rays are being emitted in scanning room 10. Preparation and depreparation room 12 provides sufficient area for preparing a patient on a cart 20 for scanning while the immediate patient is being X-rayed in scanning room 10. Preparation and depreparation room 12 has end and side magnetic locking apparatus 28 and 30 for holding a cart 20, shown in phantom outline, immobile while the patient is being prepared and depreparated. Utility room 16 provides space for auxiliary equipment.

The one-cart system (not shown) includes the following rooms: scan room, control room, and utility room. The area of the overall system is 670 sq. ft. A separate preparation room is not included in this system since this system is designed for minimum space allocation. Patient throughput rates are, therefore, not as efficient as in the two-cart and three-cart systems.

VISIBILITY AND ACCESSIBILITY

The long axis of the scanning gantry is in rotation of 13° with the long axis of the control console. The technician's view of the patient on the scanner is maximized by careful positioning of the control console as discussed previously. Observation of the patient on the scanner by the technician is provided by an observation window (lined with lead to provide radiation protection) between the scanner and the control rooms. The window is positioned at the control console where the technician sits. The size of the window is 60 inches × 36 inches. The base of the window is 43 inches above the floor. The scanner itself is in parallel configuration with the exterior wall of the scan room. Rotation of the gantry with respect to the walls for cart access is not required in the one-cart system since the mobile cart remains positioned on the lift island most of the time. A second mobile cart is stored in the scan room and it may be used for bringing non-ambulatory patients to the system. The door from the external environment to the scan room must be a minimum of 3feet 6 inches for cart access and must be positioned to facilitate the access of the mobile bed cart to the scanner.

CRITERIA FOR APPLICATION OF THE ONE-CART SYSTEM

The one-cart system is designed for sites where only a minimum of space is available. Preparation of the patient must be done at the scanner. Locations of both the patient waiting areas and dressing areas as well as the radiologist offices should be coordinated with the location of the system in order to improve patient processing times.

The two-cart system includes the following four rooms: scan room, control room, utility room and preparation room. The area of the entire system is 1030 sq. ft. The efficiency of the overall system is determined by the layout of the rooms according to visibility and accessibility.

VISIBILITY AND ACCESSIBILITY

The scanner gantry is in parallel configuration with the control console. The center line axis of the lift island is positioned to the right of the center line axis of the console in order that patient visibility is maximized. Observation of the patient on the scanner by the technician is provided by an observation window (lined with lead to provide radiation protection) between the scanner and control rooms. The window is positioned at the control console where the technician sits. The size of the window is 60 inches × 36 inches. The base of the window is 43 inches above the floor. The orientation of the gantry itself is rotated through approximately 18° with respect to the exterior wall. Rotation of the gantry provides less difficult cart access for both carts in the preparation room. (Note that if the gantry were aligned parallel with the exterior wall, the angle between the patient preparation area and the lift island area would be increased and thus cart access would be more difficult.)

CRITERIA FOR APPLICATION OF THE TWO-CART SYSTEM

Remote preparation of the patient is possible due to the use of two mobilized carts in a separate preparation room. For maximum efficiency of the two-cart system, the total time of the preparation and depreparation time segments should be no larger than the total time of the scan time segment. This particular time segment relationship will provide a more efficient flow of patients through the scanner.

Preparation of the patients can be monitored by the technician at the control console by use of a second observation window between the control room and the preparation room. The window is placed at 90° to the scanner-control room window. The computer cabinets are positioned less than 4 feet away from the control console. An area including a desk and a file cabinet behind the computer cabinets is provided for the equipment service technician. The staff entrance from the external environment is provided in this area.

An additional review console is provided for the radiologist at the end of the control room near the entrance into the waiting area of the patient preparation room. This positioning of the review console provides the radiologist access to the technician at the control console and visibility of the patient in scan. Storage is provided along the wall near the review console.

The patient preparation room consists of the mobile bed cart area and an area which may be used as either a dressing room or a waiting area. Which type of area you use it as depends upon your patient population and upon the facilities already present in the general area of your system. A dressing area is needed if you primarily service outpatients and/or if you do a large amount of body scanning. A waiting area improves the overall efficiency of your system.

The three-cart system (not shown) is the optimum plan for the scanner. The size of the whole system is 1575 square feet. The system includes the following rooms: scan room, control room, utility room, three cart patient preparation room, scan review room, reception-waiting room, patient dressing room and staff lavatory.

VISIBILITY AND ACCESSIBILITY

The configuration of both the control console and the mobile bed carts to the scanner gantry determines the placement of the other components of the system. The center line of the gantry is rotated at 20° from parallel placement with the control console. The three carts are placed in parallel positioning to the island on the gantry, at 32° rotation to the island, and at 64° rotation to the island. These placements afford the technician optimum and efficient manuevering of the carts. The three preparation areas are separated by structural walls and curtains to provide privacy to the patients waiting for scan.

The mobile carts enter into the scan room through 3 feet 6 inches doors which open at the head of the mobile cart.

CRITERIA FOR APPLICATION OF THE THREE-CART SYSTEM

Remote preparation and depreparation of the patient is possible due to the use of three mobile bed carts. The three cart system is designed for use in hospitals where there is wide variability in the type of patient population. This system accommodates the variability of the human element in patient processing, the variability of protocol on the use of contrast, and other factors.

The review area contains an additional console where the radiologist can review scans of the patient being scanned or any previous patient scans. For optimum efficiency of the system, the radiologist can use this area as his office. The radiologist is then available for scan review and contrast injection.

The waiting area contains desk and files for the receptionist and can seat seven persons at a time. The seating available in the waiting area should be determined by consideration of the ratio of the out-patient population served to the in-patient population served and also the time intervals between scheduled appointments.

The patient dressing room contains a toilet and sink. Accessibility by wheelchair-bound patients is provided by increased area and doorway.

MOBILE BED CART DIMENSIONS

The mobile bed cart measures 80 inches × 28 inches × 31 inches. Side rails are extended along the total 80 inches length on both sides of the cart.

WORKING SPACE

Minimum clearances around the cart in position in the preparation area are as follows: a minimum of 2 feet on each side of the cart is recommended as working space for the technician and other staff. A clear space of 3 feet along the length on each side of the cart is recommended as optimum working space. When the side rails are down, they occupy 9 inches on either side of the cart.

MANEUVERING THE CART

Handles are situated at either end of cart for efficient maneuvering by the technician. In the patient preparation area, a magnetic dock will assure proper orientation of the cart in the area. The path of the cart from the preparation area to the scanning gantry lift island should require the least amount of maneuvering by the technician. The most efficient path is one which requires starting the cart in motion, guiding it along a straight line, and stopping it at the scanning gantry. Handles are provided at the head end of the cart to facilitate the exit of the cart from the scanner to the preparation area.

PATIENT COMFORT AT THE SCANNER AND IN THE PREPARATION AREA

A chair should be provided in the periphery of the preparation area work space for any persons accompanying the patient. A model or graphic explaining the scanning procedure should be provided in the preparation area in order to acquaint the patient with the process he is undergoing and to ease any discomfort on his part. A mobile of bright colors or an interesting photograph should be provided above the scanner so that the patient will not become bored while waiting for scanning.

PLACEMENT OF MOBILE BED CARTS

Specific areas should be designated for the location of the cart within the preparation area. Inlaid tile stripes (or printed lines) should define the perimeter of the cart. To protect the wall surface from being scratched or marked by the mobile carts, a 4 inches protective strip should be installed at a centered height of 31 inches.

STORAGE

Work surface table tops should be a minimum of 10.5 square feet. Work tables should be positioned near the mobile bed carts and should be accessible at a height of 33¾. Storage space of drawers and cabinets for each cart should be a minimum of 32 cubic feet. Materials commonly stored are sheets, planks, an alternate head holder, various contrast media, syringes, and emergency equipment.

Figure 2:
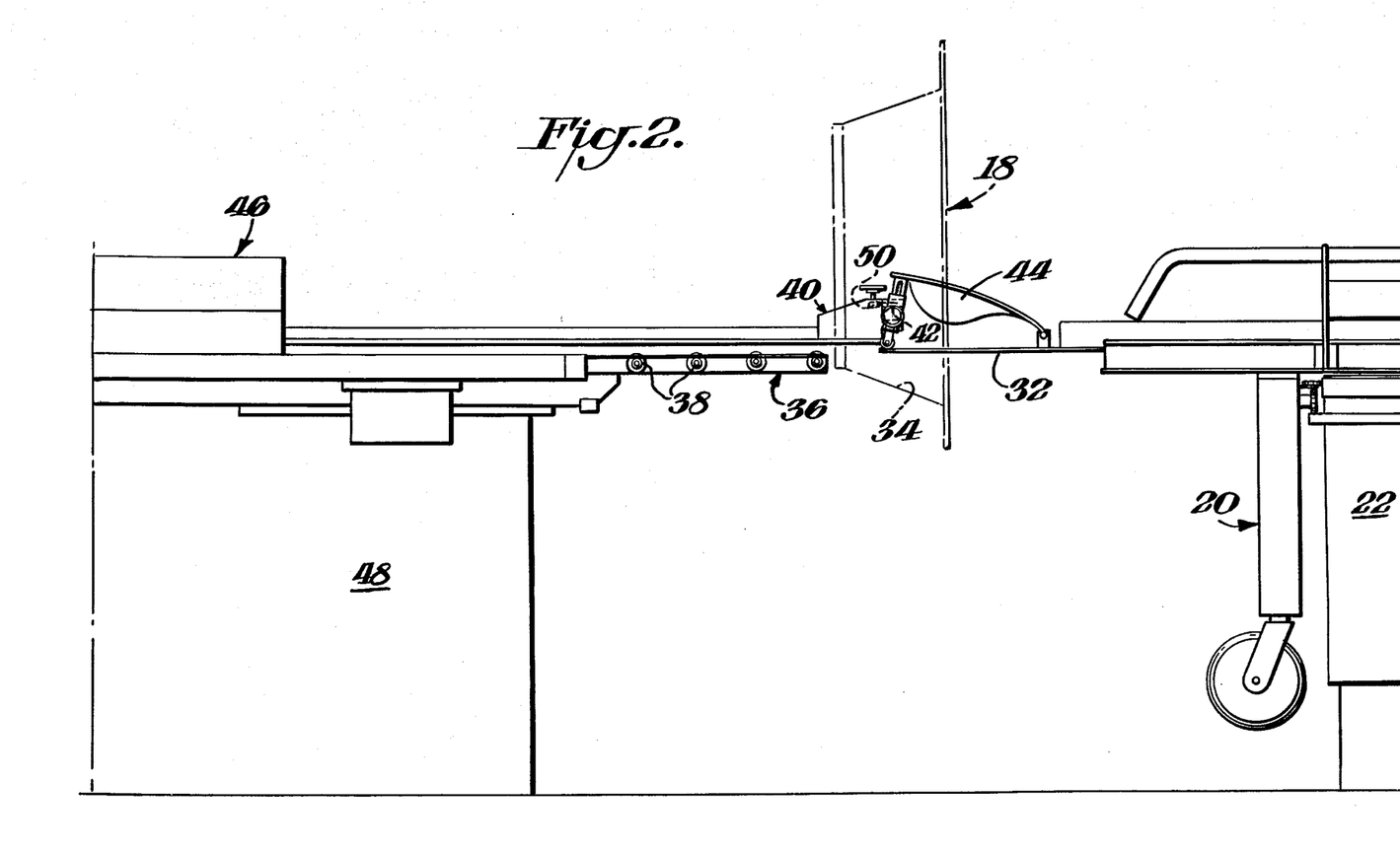
FIG. 2 is a side elevational view showing a portion of the cart in the extended position for scanning.

Details of cart 20 are shown in FIGS. 2–6. FIG. 2 shows cart 20 elevated on island 22 in proper vertical alignment for X-raying a patient (not shown) supported on cart 20 by operation of scanner 18. FIG. 2 shows extended X-ray-translucent pallet portion 32 disposed within aperture 34 of scanner 18. Pallet support 36 in back of aperture 34 is deployed for disposition under pallet portion 32 for holding it immobile during scanning.

Rear pallet support 36 includes a roller board 38 disposed adjacent scanning tunnel or aperture 34 over which translucent pallet portion 32 is disposed during scanning. Translucent pallet portion 32 is moved out over board 38 after engagement of clamping assembly 40 over ball 42 on head rest assembly 44 and subsequent retraction to the left within retracting unit 46 shown at the left side of FIG. 2. Rear pallet support 36 is disposed at a fixed scanning level on pedestal 48. Switch 50 on ball clamping assembly 40 allows pallet portion 32 to be extended when clamping assembly 40 is engaged with ball 42 on head support 44.

FIGS. 3–6 show details of cart 20. Cart 20 includes a table 52 mounted on wheeled undercarriage 54 having front and rear support panels 56 attached under table 52. Longitudinal traversing pallet assembly 58 is mounted in a central portion of table 52 for supporting a patient (not shown) and positioning him relative to scanner 18.

Figure 3:
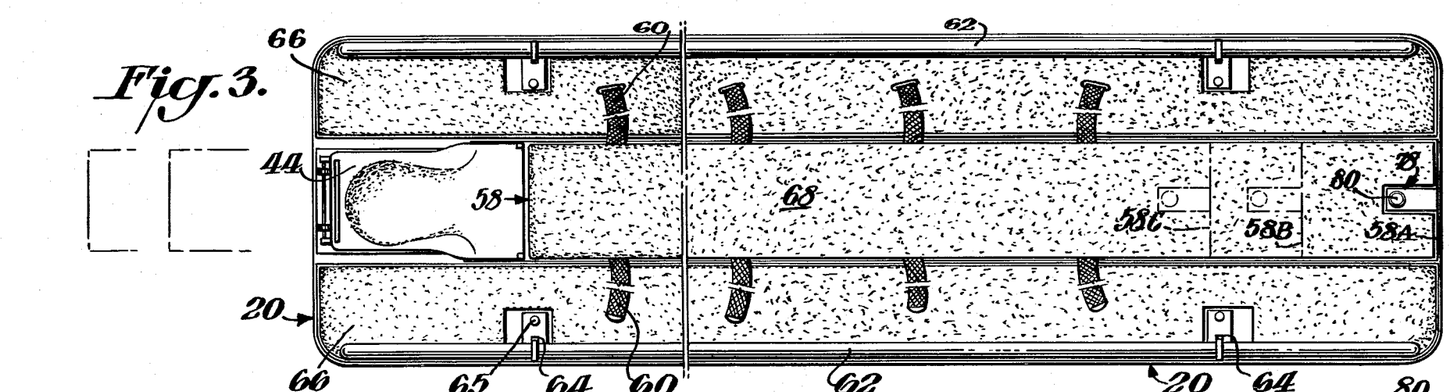
FIG. 3 is a top plan view of the patient supporting cart shown in FIGS. 1 and 2 with the pallet in various longitudinal positions.

FIG. 3 shows straps 60 for holding a patient immobile on pallet assembly 58 and retractable side rails 62 which can be grasped for moving the cart and retaining a patient on it. Rails 62 are raised and lowered in sockets 64 which may be of conventional pin and slot type. Pads 66 are disposed on the outer portions of table 52, and pad 68 is disposed on traversable pallet section 58 to shield the patient from the hard metal surfaces. Pallet section 58 is shown in several longitudinal positions designated 58a, b and c.

Movable pallet section 58 is actuated by control handle 78 having a reciprocable upper control pin 80 mounted on control box 82 attached to pallet 58. Control handle 78 is used for manually moving pallet section 58 from locked position 58a to intermediate position 58b in which a slide plate is engaged for freeing the X-ray translucent portion 32 for movement into extended positions as later shown. Position 58c is a further manually set position of pallet section 58 and control handle 78 in which a motor traversing drive is engaged. FIG. 3 also shows four sockets 65 for holding rods (not shown) which may be used to support IV sets for contrast injections and for general IV use if necessary. FIG. 3 also shows head rest 44 which may adjustably support a patient's head in a comfortable position for scanning his brain or other portions of the body.

Control handle 78 may be engaged with chain 126 for precision positioning of pallet 58 and may be used to manually move pallet 58 for gross positioning and rapid emergency movement.

Figure 4:
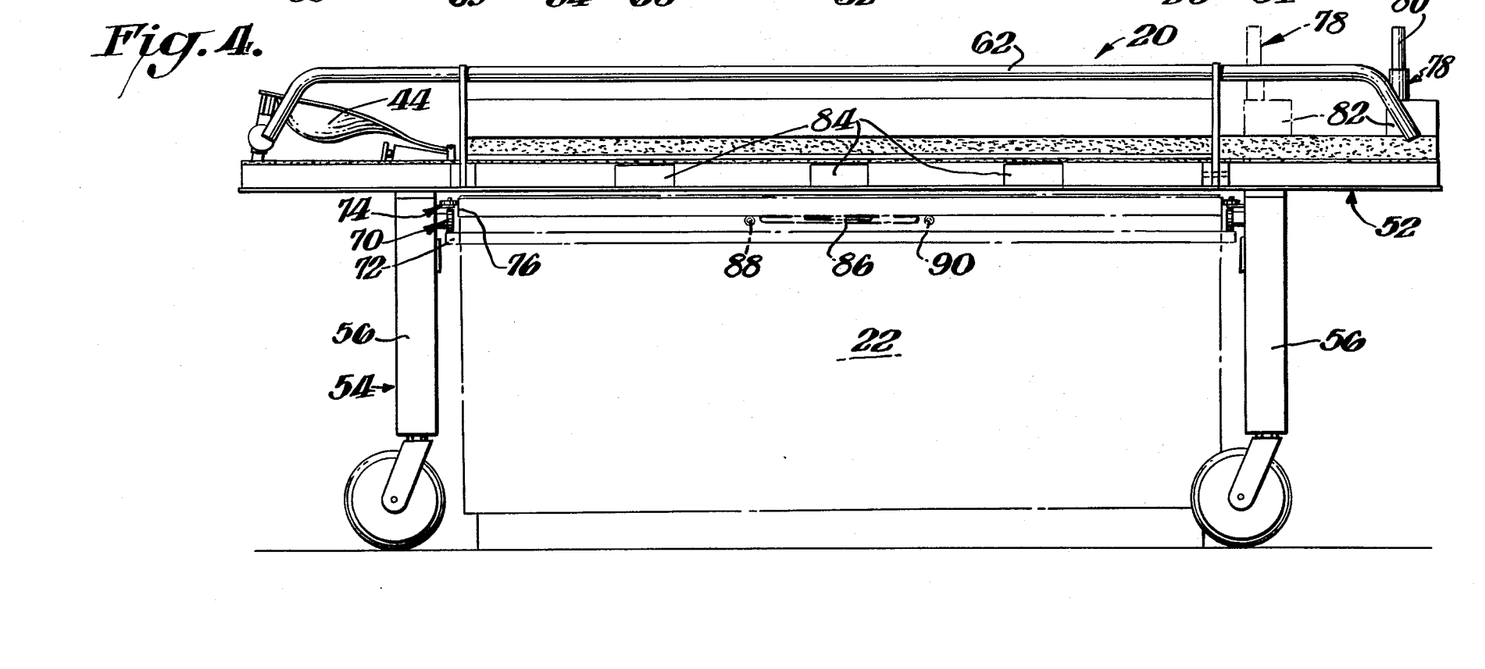
FIG. 4 is a side elevational view of the cart shown in FIGS. 1-3.

FIG. 4 shows cart 20 positioned over island 22 so that it can be elevated upon it. Horizontal roller assemblies 70 extending within support panels 56 rest upon island track 72, and vertical roller assemblies 74 within support panels 56 engage end wall 76 of island 22 to precisely adjust the position of cart 20 relative to island 22 so that it can be locked to it before elevation upon it.

FIG. 4 also shows three ferromagnetic plates 84 in the side of table 52 for engaging with magnetic docking apparatus 30. FIG. 4 shows lever 86 for locking and unlocking cart 20 to island 22 by pins which are later described. Red light 88 glows when the cart is unlocked. A green light 90 glows when the cart 20 is locked to island 22.

Figure 5:
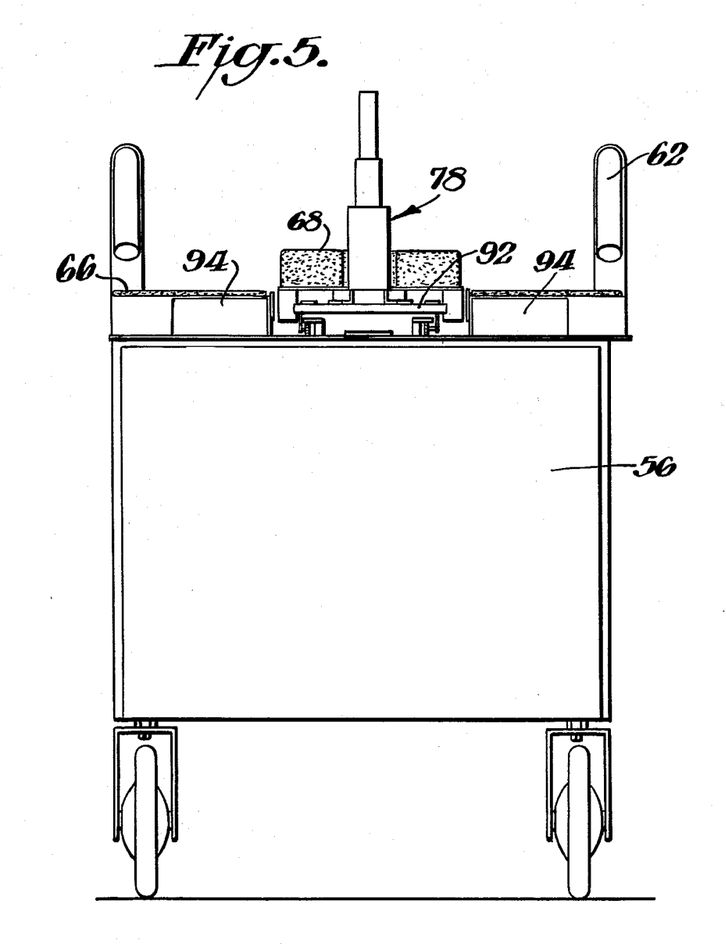
FIG. 5 is a right end elevational view of the cart shown in FIGS. 3 and 4.

In FIG. 5 is shown longitudinally moving roller supported plate 92 to which control handle 78 is attached for manual traversing and control movement. FIG. 5 shows rear ferromagnetic plates 94 utilized for engaging cart 20 with magnetic docking apparatus 28 shown in FIGS. 1, 13 and 14.

Figure 6:
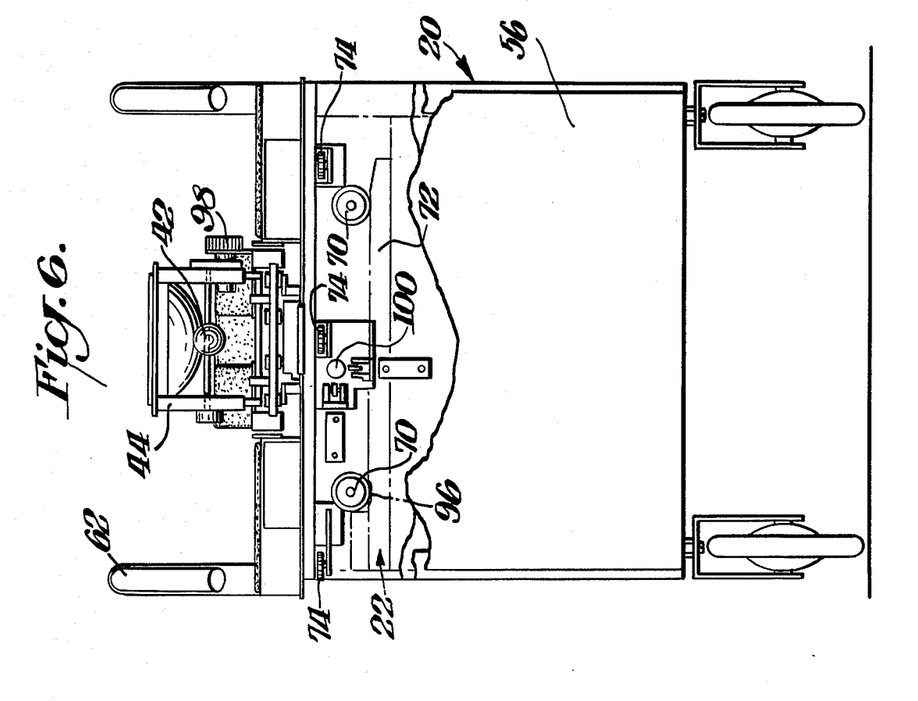
FIG. 6 is a left end elevational view of the cart shown in FIGS. 3-5.

FIG. 6 shows indentation 96 for indexing the engaged position of roller 70, later described in more detail in FIG. 10. Cart 20 is lifted by the upward movement of track 72 under rollers 70. Knob 98 shown in FIG. 6 actuates the raising and lowering of head rest 44. FIG. 6 also shows ball 42 which is grasped by clamping assembly 40 for moving X-ray translucent pallet portion 32 into the scanning position. FIG. 6 further shows locking pin 100 used for securing cart 20 on island 22 as later described in detail in conjunction with FIGS. 7–9.

Figure 7:
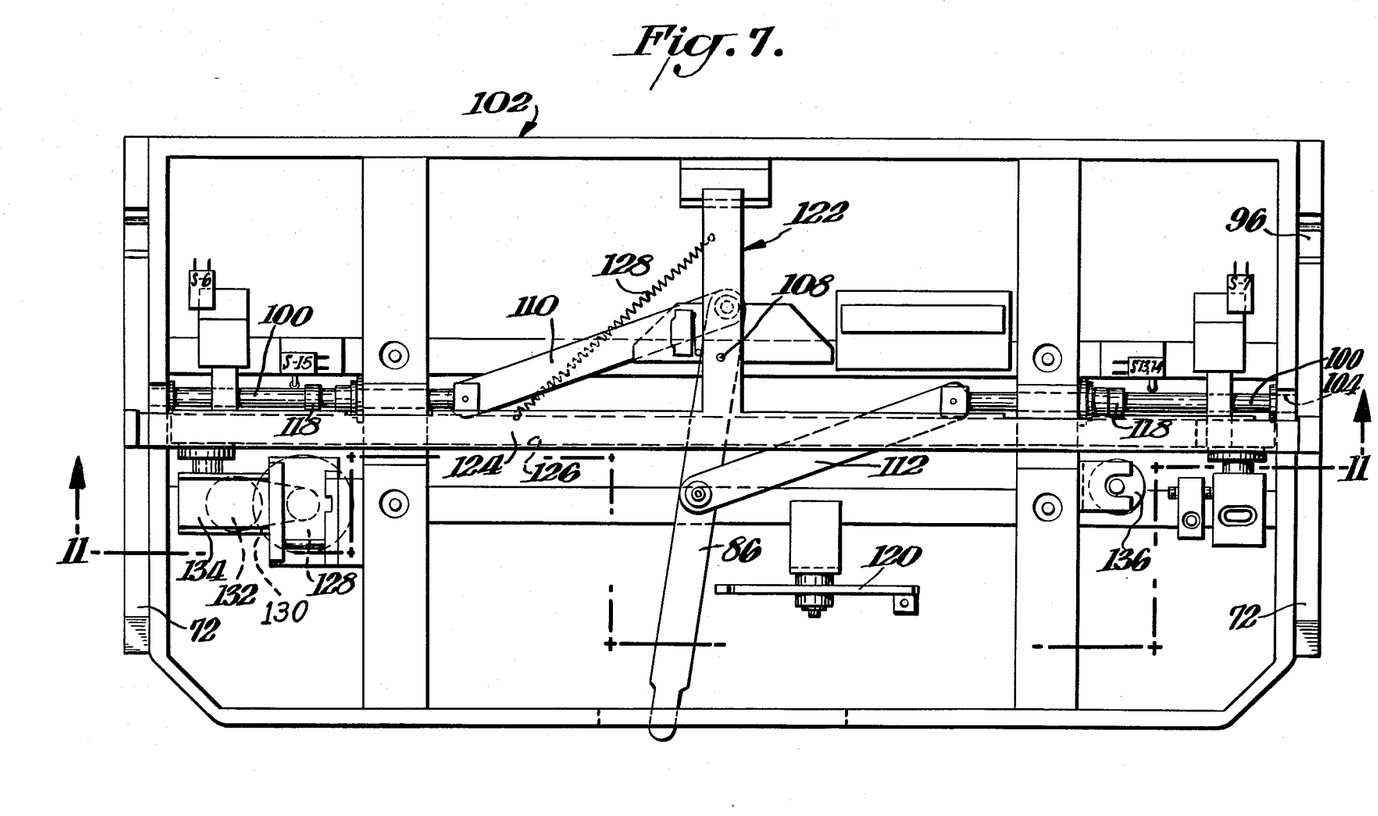
FIG. 7 is a top plan view of the island support shown in FIG. 1 in a disengaged position from the cart.
Figure 8:
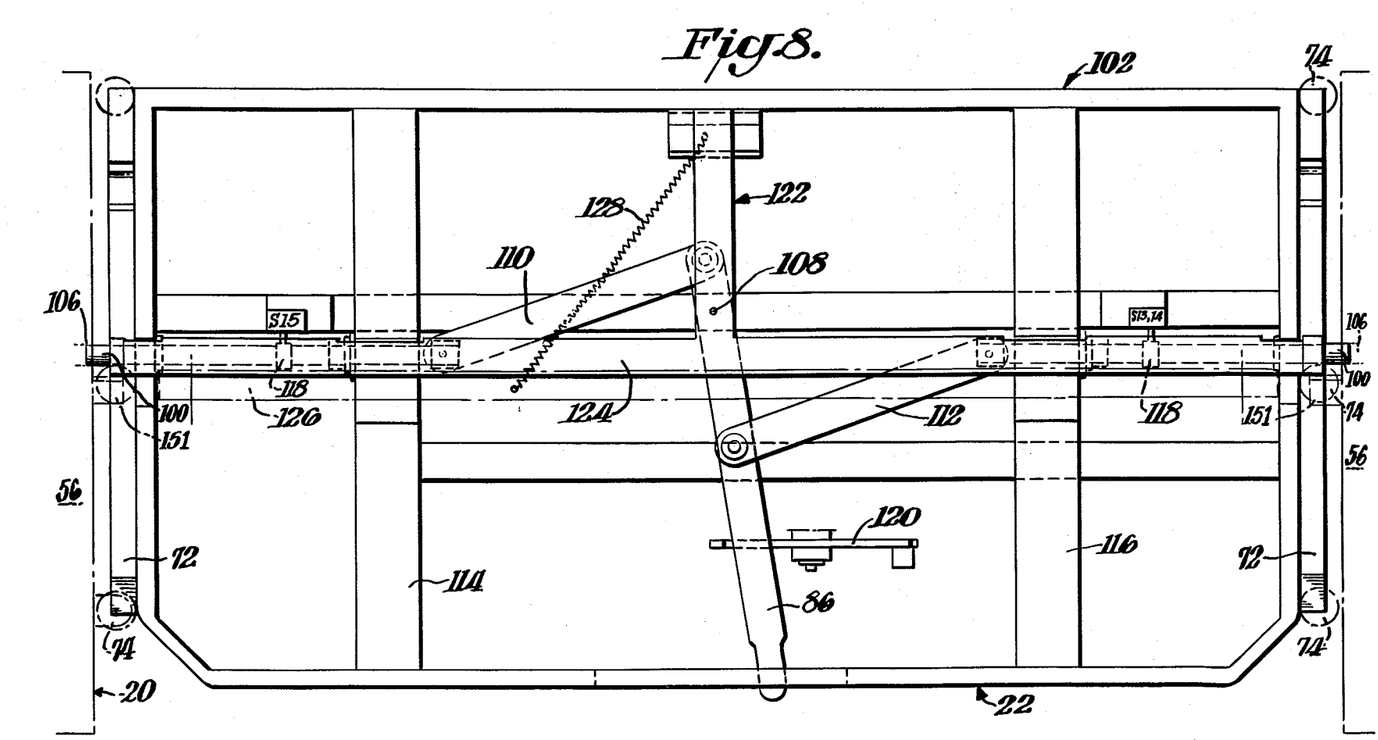
FIG. 8 is a top plan view of the island shown in FIG. 7 engaged and locked to a cart.
Figure 9:
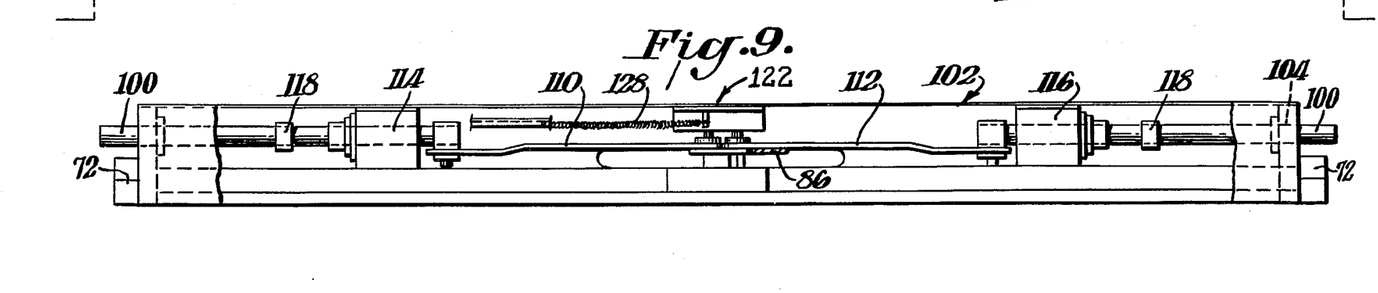
FIG. 9 is a side elevational view partially broken away illustrating the locking mechanism shown in FIG. 8.
Figure 10:
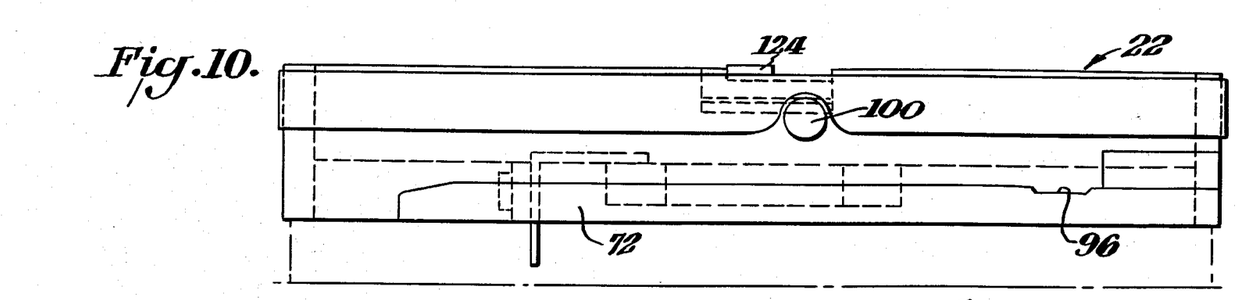
FIG. 10 is an end elevational view of the island and locking mechanism shown in FIGS. 7-9.

Locking frame 102 on island 22 is shown in FIGS. 7–9. Locking pins 100 extend through apertures 104 in the ends of locking frame 102 into engagement with corresponding apertures 106 in undercarriage panels 56 of cart 20 as shown in phantom outline in FIGS. 8 and 9. Locking pins 100 are actuated by lever 86 rotatably pivoted about pin 108 attached to frame assembly 102. Lever 86 is rotatably connected through operating links 110 and 112 to locking pins 100 which are reciprocated by lateral movement of lever 86. The lateral movement of pins 100 is guided by bearing assemblies 114 and 116. Limit switches S13 and S15 are actuated by contact of sleeves 118 to allow island 22 to lift cart 20 when pins 100 are engaged to lock cart 20 to island 22. Limit switches S6 and S7 coordinate other control aspects of the apparatus.

Figure 11:
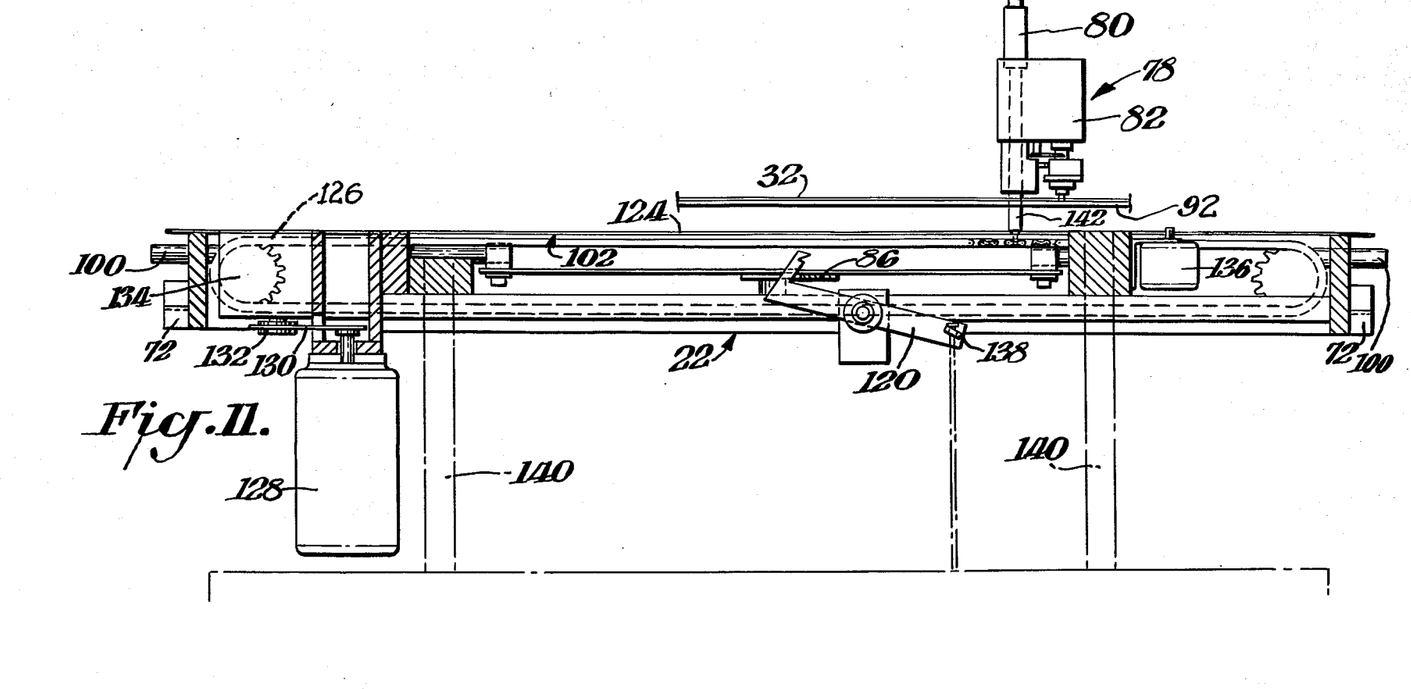
FIG. 11 is a cross-sectional view in elevation taken through FIG. 7 along line 11—11.

T-shaped link 122 is shown in FIG. 7 with its central portion 124 disposed over traversing sprocket chain 126. Spring 128 urges T-shaped link 122 into its sprocket-covering position. Sprocket chain 126 is actuated by motor 128, which is for example a stepper motor of the type used for actuating aircraft wing flaps. Motor 128 is connected to sprocket chain 126 through drive chain 130, clutch 132 and reducing gear 134. Switch 50 as shown in FIG. 2, senses the coupling of clamp 40 and head support 44 and energizes solenoid 136 as shown in FIG. 7 and FIG. 11. Thereby releasing plate 92 from its locked 58A position.

FIG. 8 shows locking pins 100 in the position in which they engage undercarriage panels 56 of cart 20 in conjunction with coordinated positions of lever 86. Lever 86 is in the position in which it can be engaged by locking lever 120, which is connected to island 22 by connecting lug 138 as shown in FIG. 8 and FIG. 11. Locking lever 120 is actuated to engage lever 86 when the island is elevated, such as two inches above its lowered position as shown in FIG. 11. FIG. 8 also shows T-shaped guard link 122 moved aside by contact of arms 151 mounted on undercarriage panels 56 of cart 20 from sprocket chain 126 to permit it to be engaged by a pin 142 on the lower end of pallet handle 78 as shown in FIG. 11.

FIG. 11 shows sprocket chain 126 and its driving mechanism. FIG. 11 also shows locking frame 102 lifted upon elevating rods 140 by a suitable lifting mechanism (not shown) which for example may be of the lead screw and nut type.

Figure 12:
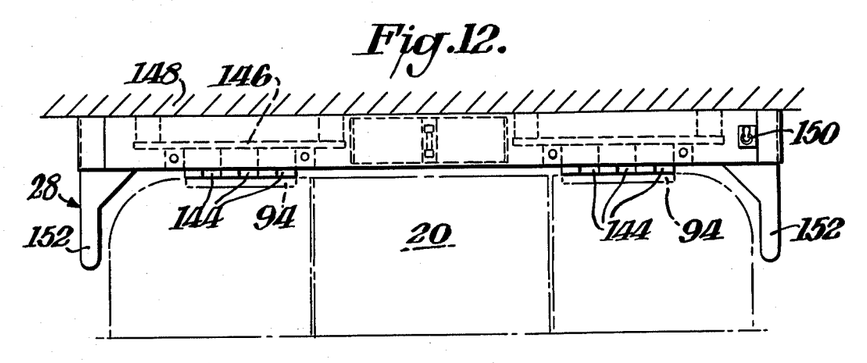
FIG. 12 is a top plan view of the magnetic docking assembly of FIG. 1 with engaged cart shown in phantom outline.
Figure 13:
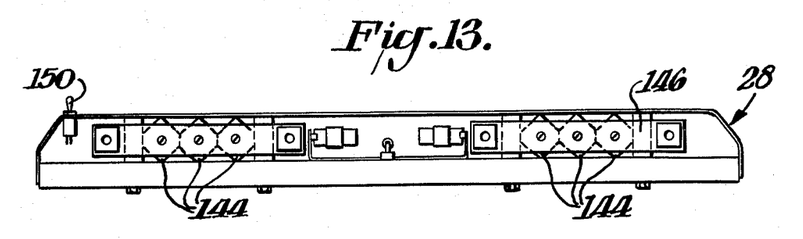
FIG. 13 is a rear elevational view of the magnetic docking assembly shown in FIG. 12.

Magnetic docking assembly 28 is shown in FIGS. 12 and 13. Docking assembly 28 is used for engagement with the end of cart 20 as shown in FIG. 1. A similar but longer assembly 30 may be used for engaging the side of cart 20 as also shown in FIG. 1. Magnetic assembly 28 has two arrays of magnetic armatures 144 mounted in frame 146 which is attached to a wall 148. Armatures 144 are controlled by switch 150 which energizes and deenergizes them. FIG. 12 shows locating arms 152 which guide the end of cart 20 into engagement with magnetic docking assembly 28 with ferromagnetic plates 94 disposed adjacent armatures 144. When armatures 144 are energized, cart 20 is securely held against magnetic docking assembly 28 to hold it immobile while a patient is being prepared for or deprepared from a scanning operation. Magnetic assemblies 28 and magnetic plates 94 may also be used in conjunction with any type of hospital cart for holding it immobile while a patient is disposed upon it.

I claim:

1. A system for handling patients to be X-rayed on a tomographic scanner having a vertically adjustable patient-supporting island disposed adjacent its scanning tunnel comprising a cart for transporting the patient to and from the island, the cart having a longitudinally-movable patient-supporting pallet mounted upon it, a locking frame mounted upon an elevating portion of the island, the cart having an under-portion constructed and arranged for disposition over the locking frame when it is disposed in a lower position, the locking frame and underportion being constructed and arranged for engaging the locking frame with the under-portion of the cart to elevate it, securing means locking the locking frame with the under-portion of the cart when it is engaged therewith, precision longitudinal traversing drive means in the island for causing the longitudinally-movable pallet to move itself and the patient supported upon it into the scanning position, coordinating means on the island and cart for engaging the pallet with and disengaging it from the precision longitudinal traversing drive means, and control means for operating the longitudinal traversing drive means to position the patient for scanning.

2. A system as set forth in claim 1 wherein a plurality of carts are provided whereby a patient may be prepared and recover from scanning while another patient is being scanned.

3. A system as set forth in claim 2 wherein at least two of the carts are provided.

4. A system as set forth in claim 2 wherein at least three of the carts are provided.

5. A system as set forth in claim 1 wherein the longitudinal traversing drive means includes motorized traversing means.

6. An apparatus for handling patients to be X-rayed on a tomographic scanner having a vertically adjustable island disposed adjacent the scanner comprising a cart for transporting the patient to and from the island, the cart having a longitudinally movable patient-supporting pallet section, a locking frame mounted upon a vertically-movable portion of the island, an under-portion of the cart being constructed and arranged for disposition over the island and locking frame when the island is disposed in its lowest position, the locking frame and under-portion being constructed and arranged for engaging the locking frame with the under-portion of the cart when the island is to be elevated, securing means locking the locking frame with the under-portion of the cart when it is engaged therewith, precision longitudinal traversing drive means in the island for causing the longitudinally movable pallet to move into the scanning position, coordinating means on the island and cart for engaging the pallet with the precision longitudinal traversing drive means in the island, and control means operating the precision longitudinal-traversing drive means to adjust the longitudinal position of the pallet and patient upon it.

7. An apparatus as set forth in claim 6 wherein the pallet is disposed in a midsection of an upper portion of the cart.

8. An apparatus as set forth in claim 7 wherein interlocking means is provided for preventing the pallet from being moved unless the cart is engaged with and lifted upon the island.

9. An apparatus as set forth in claim 8 wherein the securing means includes reciprocating pins mounted on the locking frame and corresponding apertures in the cart.

10. An apparatus as set forth in claim 9 wherein the cart has an undercarriage, and the apertures are disposed within the undercarriage.

11. An apparatus as set forth in claim 10 wherein the precision longitudinal-traversing drive means comprises a sprocket chain, and the coordinating means includes a movable rod which is engagable with and disengagable from the sprocket chain.

12. An apparatus as set forth in claim 11 wherein the control means includes a control handle and the rod is attached to the control handle.

13. An apparatus as set forth in claim 6 wherein a magnetic docking means is provided, and ferromagnetic means are disposed on the cart for permitting it to be magnetically engaged with the magnetic docking apparatus for immobilizing the cart.

14. An apparatus as set forth in claim 6 wherein aligning rollers are provided on the cart for movably engaging the cart with portions of the island for adjusting its position relative thereto.

15. An apparatus for handling patients to be X-rayed on a tomographic scanner having a vertically-adjustable island having precision longitudinally-traversing drive means disposed adjacent the scanner comprising a cart for of transporting the patient to and from the island, the cart having a longitudinally movable patient-supporting pallet section, an under-portion of the cart being constructed and arranged for disposition over the island when the island is disposed in its lowest position, the under-portion being constructed and arranged for engaging the island with the under-portion of the cart when the island is to be elevated, securing means on the island and cart for locking the under-portion of the cart to the island when it is engaged therewith, coordinating means on the cart for engaging the pallet with the precision longitudinal traversing drive means in the island, and control means on the cart for operating the precision longitudinal-traversing drive means to adjust the longitudinal position of the pallet and patient upon it.

16. An apparatus as set forth in claim 15 wherein the pallet is disposed in a midsection of an upper portion of the cart.

17. An apparatus as set forth in claim 16 wherein interlocking means is provided for preventing the pallet from being moved unless the cart is engaged with and lifted upon the island.

18. An apparatus as set forth in claim 17 wherein the securing means includes apertures in the cart.

19. An apparatus as set forth in claim 18 wherein the cart has an undercarriage, and the apertures are disposed within the undercarriage.

20. An apparatus as set forth in claim 19 wherein the coordinating means includes a movable rod which is engagable with and disengagable from the precision longitudinal-traversing means.

21. An apparatus as set forth in claim 20 wherein the control means includes a control handle, and the rod is attached to the control handle.

* * * * *